United States Patent [19]

Huan et al.

[11] Patent Number: 5,047,567
[45] Date of Patent: Sep. 10, 1991

[54] HETEROPOLYOXO VANADIUM COMPOUNDS CONTAINING MOLECULAR ANIONS AND THEIR STRUCTURE

[75] Inventors: Guohe Huan, Washington; Allan J. Jacobson, Princeton, both of N.J.

[73] Assignee: Exxon Research & Engineering Company, Florham Park, N.J.

[21] Appl. No.: 583,406

[22] Filed: Sep. 17, 1990

[51] Int. Cl.$^5$ ............................ C07F 9/00; C07F 9/02; C07F 9/70

[52] U.S. Cl. ........................................ 556/42; 556/43; 556/13; 556/19; 556/64; 556/70; 556/71; 556/72; 556/76; 556/30; 502/209

[58] Field of Search ............ 556/42, 43, 13, 19, 556/64, 68, 70, 71, 72, 76, 30; 502/150, 152, 155, 164, 208, 209

[56] References Cited

U.S. PATENT DOCUMENTS 4,465,636 8/1984 Abramson et al. ................ 556/42
4,822,925 4/1989 Briggs et al. ................ 556/42 X
4,937,338 6/1990 Flohr et al. ................ 556/42 X Primary Examiner—Arthur C. Prescott
Attorney, Agent, or Firm—Sidney Persley; Joseph J. Dvorak

[57] ABSTRACT

A solid composition of matter comprising heteropolyoxo vanadium oxide compounds of the general formula: $(R'_4N)_xH_y(VO_b)_a(RQO_3)-nH_2O)$ wherein $(VO_b)_a(RQO_3)$ is a molecular anion; R' is a substituted or unsubstituted monovalent organic group covalently bound to nitrogen to form a tetraorgano ammonium cation $(R'_4N)$; R is a substituted or unsubstituted monovalent organic group covalently bound to Q to form an organophosphorus or organoarsenous group; R and R' are selected from the group consisting of $C_1$–$C_{20}$ alkyl, aryl, hetero alkyl, hetero aryl or mixtures thereof; Q is a phosphorus or arsenic atom; a is about 1.0 to about 3.0; b is about 1.0 to about 2.0; $(x+y)$ are determined by the vanadium oxidation state (m) where $(x+y)$ equals $(2ab+2)-ma$ and where $(x+y)$ and x can not equal zero; and n is zero or a positive number.

13 Claims, 6 Drawing Sheets

HETEROPOLYOXO VANADIUM COMPOUNDS CONTAINING MOLECULAR ANIONS AND THEIR STRUCTURE

BACKGROUND OF THE INVENTION

1. Field of the Invention

The invention relates to heteropolyoxo vanadium compounds of the general formula:

$$(R'_4N)_x H_y (VO_b)_a (RQO_3) \cdot nH_2O$$

2. Description of the Prior Art

A number of heteropolyoxo vanadium compounds are found in the open and patent literature. For example, heteropolyoxo compounds containing molecular anions of vanadium atoms are described in V. W. Day et al., "Synthesis and Characterization of a Soluble Inclusion Complex $CH_3CN(V_{12}O_{32}{}^{4-})$", J. Am. Chem. Soc., Vol. Ill, pp. 5959-5961 (1989); A. Muller et al., "$[V_{19}O_{41}(OH)_9]^{8-}$, An Ellipsoid-Shaped Cluster Anion Belonging to the Unusual Family of $V^{iv}/V^v$ Oxygen Clusters", Agnew. Chem. Int. Ed. Engl., Vol. 27, pp. 1719-1721 (1988); G. K. Johnson et al., "Existence and Structure of the Molecular Ion 18-Vanadate (IV)", J. Am. Chem. Soc., Vol. 100, pp. 3645-3646 (1978); A. Muller et al., "Spherical Mixed-Valence $[V_{15}O_{36}]^{5-}$, an Example from an Unusual Cluster Family", Agnew. Chem. Int. Ed. Engl., Vol. 26, pp. 1045-1046 (1987); A. Bino et al., "Molecular Structure of a Mixed Valence Isopolyvanadate", Inorg. Chem., Vol. 21, pp. 429-431 (1982); Y. Hayashi et al., "The First Vanadate Hexamer capped by four Pentamethyl-Cyclopentadienyl -rhodium or -iridium Groups", Chem. Lett., pp. 425-428 (1989); M. V. Capparelli et al., "Protonation sites in the Decavanadate Ion. X-ray Crystal Structure of Tetrakisadenosinium Dihydrodecavanadate (V) Undecahydrate", J. Chem. Soc. Chem. Commun., Vol. pp. 776-777 (1986). However, these references do not disclose molecular anions containing phosphorus or arsenic atoms bonded to oxygen atoms wherein the oxygen atoms are bonded to vanadium atoms.

Heteropolyoxo vanadium compounds containing phosphorus or arsenic atoms or other heteroatoms bound to oxygen atoms which are bonded to vanadium atoms have been reported in, for example, R. Kato et al., "The Heteropolyvanadate of Phosphorus Crystallographic and NMR Studies", Inorg. Chem., Vol. 21, pp. 246-253, 1982; A. Muller et al., "A Novel Heterocluster with $D_3$-Symmetry Containing Twenty-One Core Atoms: $[As_6{}^{III}V_{15}{}^{IV}O_{42}(H_2O)]^{6-}$", Agnew. Chem. Int. Ed. Engl., Vol. 27, p. 1721 (1988); T. Ozeki et al., "Structure of Heptaammonium Hydrogendecavanadotetraselenite Nonanhydrate", Acta. Crystallogr., Vol. C43, pp. 1662-1665 (1987); H. Ichida et al., "Heteropolyvanadate Containing Two and Three Manganese(IV) Ions Unusual Structural Features of $Mn_2V_{22}O_{64}{}^{10-}$ and $Mn_3V_{12}O_{40}H_3{}^{5-}$", J. Am. Chem. Soc., Vol. 111, pp. 586-591 (1989); K. Nagai et al., "The Structure of Heptapotassium Tridecavana-domanganate(IV) Octadecahydrate, $K_7[MnV_{13}O_{38}] \cdot 18H_2O$", Chem. Lett., pp. 1267-1270 (1986). However, these references do not disclose molecular anions containing phosphorus or arsenic atoms bonded to oxygen atoms wherein the oxygen atoms are bonded to vanadium atoms and a monovalent organic group.

U.S. Pat. Nos. 4,268,448 issued to Franz et al.; 4,192,951 issued to Slinkard et al.; and 4,434,082 issued Murtha et al., describe heteropolyoxo vanadium compounds with molecular anions containing phosphorus or arsenic, however, these compounds either do not contain a monovalent organic group or a monovalent organic group bonded to phosphorus or arsenic atoms.

Other publications disclosing heteropolyoxo vanadium compounds include D. Rehder et al., "$[VO(O_2C\text{-}tBu)_3]$ and $[V_6O_6(\mu\text{-}O_2CPh)_9]$: Structural Characterization of a Mononuclear $V^v$ and a $(2+4)$-Nuclear $V^{IV}V_5^V$ Carboxylate Complex: Models for Vanadate Dependent Peroxidases", Agnew. Chem. Int. Ed. Engl., Vol. 28, pp. 1221-1222 (1989); Qin Chen et al., "A Cyclic Octanuclear Poyoxoalkoxyvanadate(IV) with an Oxalate-Binding Cavity", Inorg. Chem., Vol. 28, pp. 4433-4434 (1989); D. D. Heinrich et al., "Synthesis of Tetranuclear and Pentanuclear Vanadium-Oxide-Carboxylate Aggregates", J. Chem. Soc. Commun., pp. 1411-1413 (1989). However, these references do not disclose phosphorus or arsenic atoms bound to a monovalent organic group.

U.S. Pat. No. 4,518,534, issued to Johnson et al., discloses oxide compounds containing vanadium and phosphorus or arsenic with unique structures of the formula $VORAO_3 \cdot nS$, where A is phosphorous or arsenic, S is a solvent, R is an organic group and n is zero or a positive number. These compounds have layered structures comprised of infinite two dimensional networks of covalently bonded atoms, see FIGS. 2 and 3 of the Johnson, et al. reference. The networks comprise covalently bonded vanadium, oxygen and phosphorus or arsenic atoms.

It is an object of the present invention to provide solid heteropolyoxo vanadium compounds containing molecular anions composed of finite structures of covalently bonded phosphorus or arsenic atoms bonded to oxygen atoms wherein the oxygen atoms are bonded to vanadium atoms and a monovalent organic group.

It is also an object of the present invention to provide heteropolyoxo vanadium compounds containing molecular anions having novel structures.

SUMMARY OF THE INVENTION

The invention is a solid composition of matter comprising heteropolyoxo vanadium oxide compounds of the general formula:

$$(R'_4N)_x H_y (VO_b)_a (RQO_3) \cdot nH_2O$$

wherein $(VO_b)_a(RQO_3)$ is a molecular anion; R' is a substituted or unsubstituted monovalent organic group covalently bound to nitrogen to form a tetraorgano ammonium cation ($R'_4N$); R is a substituted or unsubstituted monovalent organic group covalently bound to Q to form an organophosphorus or organoarsenous group; R and R' are selected from the group consisting of $C_1$-$C_{20}$ alkyl or aryl, alkenyl, alkylnyl, haloalkyl, arylalkyl, mercaptoalkyl, aminoalkyl, carboxyalkyl, cyanoalkyl, sulfoalkyl, alkoxyalkyl, aryloxyalkyl, diketoalkyl, aryl, haloaryl, alkylaryl, aminoaryl, mercaptoaryl, carboxyaryl, cyanoaryl, sulfoaryl, alkoxyaryl, aryloxyaryl, diketoaryl or mixtures thereof; Q is a phosphorus or arsenic atom; a is about 1.0 to about 3.0; b is about 1.0 to about 2.0; the sum of x and y represent the total number of ($R'_4N$) cations and protons in the composition determined by the vanadium oxidation state (m) and are such that $(x+y)$ must equal $(2ab+2)-ma$ and $(x+y)$ and x cannot equal zero and n is zero or a positive number.

In another aspect the invention is heteropolyoxo vanadium compounds of the general formula $(R'_4N)_xH_y(VO_2)_2(RQO_3)$ $nH_2O$ wherein the molecular anion $(VO_2)_2RQO_3$ has a structure corresponding to FIGS. 3 and 4.

In another aspect the invention is heteropolyoxo vanadium compounds of the general formula $(R'_4N)_xH_y(VO_2)_{1.5}(RQO_3)$ $nH_2O$ wherein the molecular anion $(VO_2)_{1.5}(RQO_3)$ has a structure corresponding to the dodecahedron shown in FIG. 5.

DETAILED DESCRIPTION

Figure 1:
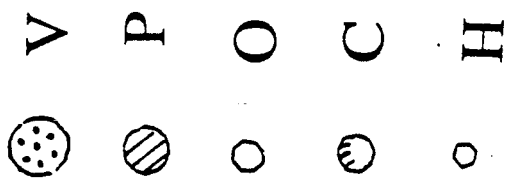
FIG. 1 shows the molecular anion of the heteropolyoxo vanadium compound in Example 1.
Figure 1:
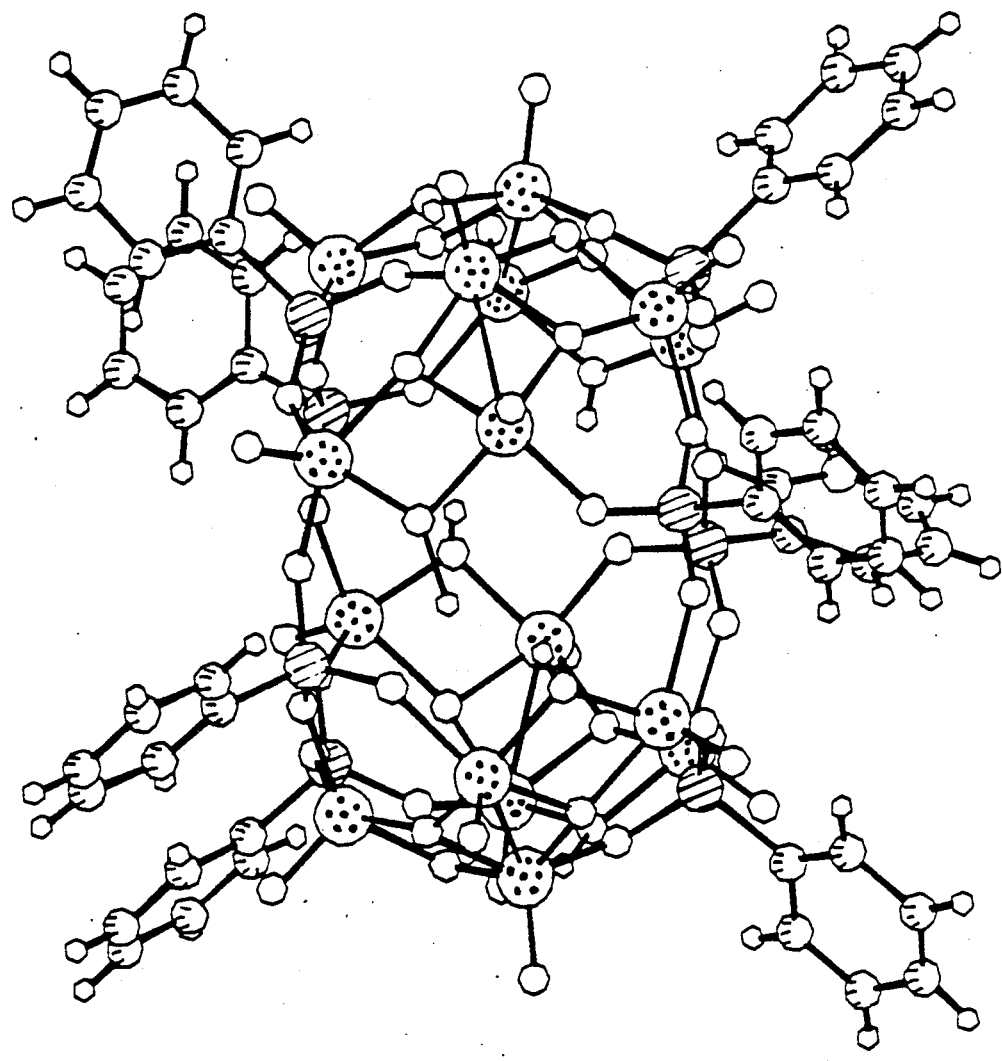
Figure 2:
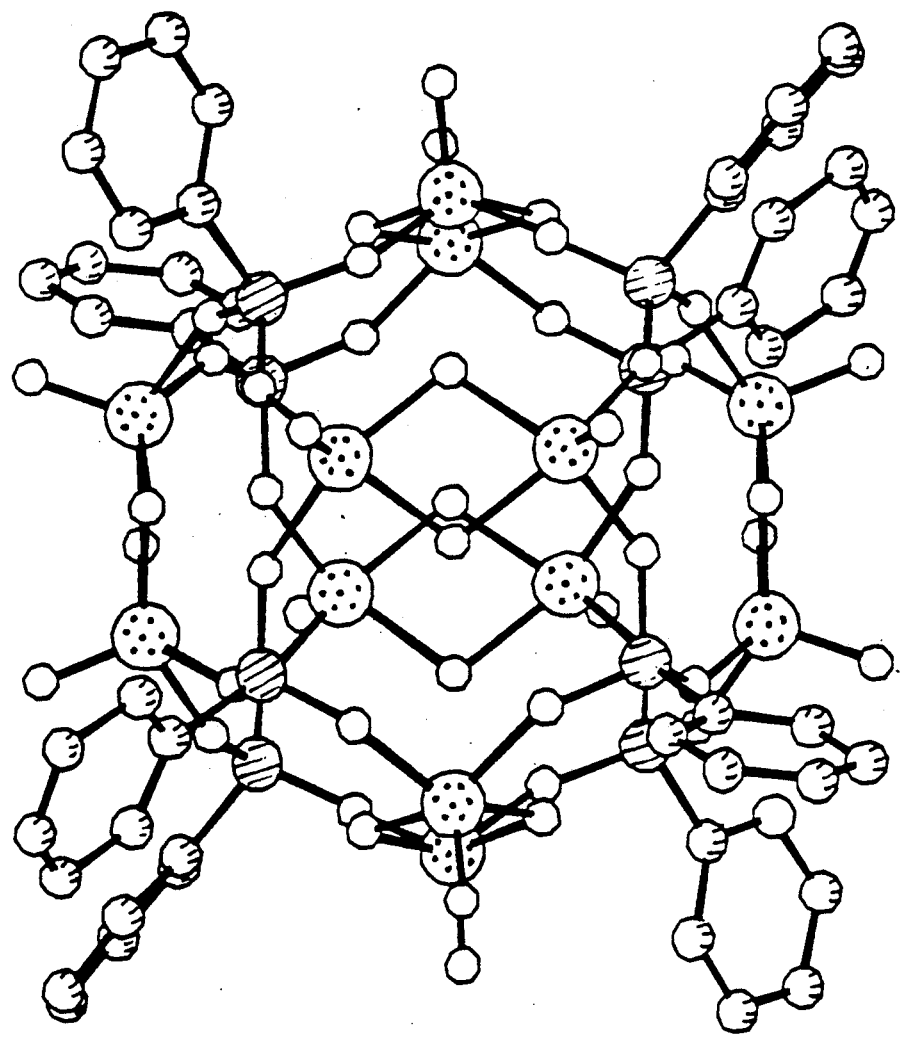
FIG. 2 shows the molecular anion of the heteropolyoxo vanadium compound in Example 7.

In the general formula $(R'_4N)_xH_y(VO_b)_a(RQO_3)\cdot nH_2O$, R is bonded to a phosphorus or arsenic atom and selected from the group consisting of, but not limited to, substituted or unsubstituted monovalent organics, such as, alkyl, alkenyl, alkylnyl, haloalkyl, arylalkyl, mercaptoalkyl, aminoalkyl, carboxyalkyl, cyanoalkyl, sulfoalkyl, alkoxyalkyl, aryloxyalkyl, diketoalkyl, aryl, haloaryl, alkylaryl, aminoaryl, mercaptoaryl, carboxyaryl, cyanoaryl, sulfoaryl, alkoxyaryl, aryloxyaryl, diketoaryl or mixtures thereof. Preferably, R is selected from phenyl, biphenyl, $C_1$-$C_4$ alkyl- or $C_1$-$C_4$-alkoxy-substituted phenyl, $C_1$-$C_{20}$ alkyl group, or mixtures thereof. More preferably R is selected from p-methoxyphenyl, p-ethoxy-phenyl, ethyl, methyl, propyl, hexyl, octyl, decyl, octadecyl, naphthyl and mixtures thereof. The preferred R groups may optionally include functional groups containing, for example, oxygen, sulfur, nitrogen, phosphorus, halogen or other atoms such as —COOR, —NH$_2$, —OH, —PR$_2$, —CN, —COOH, —SH, —SO$_3$H, more preferred are —COOR, —COOH, —OH and —CN.

In the general formula $(R'_4N)_xH_y(VO_b)_a(RQO_3)$ $nH_2O$, R' is selected from the group consisting of, but not limited to, substituted or unsubstituted monovalent organics, such as, alkyl, alkenyl, alkylnyl, haloalkyl, arylalkyl, mercaptoalkyl, aminoalkyl, carboxyalkyl, cyanoalkyl, sulfoalkyl, alkoxyalkyl, aryloxyalkyl, diketoalkyl, aryl, haloaryl, alkylaryl, aminoaryl, mercaptoaryl, carboxyaryl, cyanoaryl, sulfoaryl, alkoxyaryl, aryloxyaryl, diketoaryl or mixtures thereof. Preferably, R' is selected from phenyl, biphenyl, $C_1$-$C_4$ alkyl- or $C_1$-$C_4$-alkoxy substituted phenyl, $C_1$-$C_{20}$ alkyl group, or mixtures thereof. More preferably R' is selected from p-methoxyphenyl, p-ethoxy-phenyl, ethyl, methyl, propyl, hexyl, octyl, decyl, octadecyl, naphthyl and mixtures thereof. The preferred R' groups may optionally include functional groups containing, for example, oxygen, sulfur, nitrogen, phosphorus, halogen or other atoms such as —COOR, —NH$_2$, —OH, —PR$_2$, —CN, —COOH, —SH, —SO$_3$H, more preferred are —COOR, —COOH, —OH and —CN.

The oxide portion of the molecular anion, represented by $(RQO_3)$, may contain mixed organophosphonate or organoararsonate groups or other combinations of these groups, depending on the organic acid employed and the compound desired. For example, use of an organophosphonic acid produces a vanadium organophosphonate, whereas use of a organoarsonic acid produces a vanadium organoarsonate. Employing oxides substituted with different monovalent organic groups or employing mixtures of arsonic and phosphonic acids, for example, results in mixed compounds as described above.

The phrase "molecular anion" defines an anion containing finite structures of covalently bonded phosphorus or arsenic atoms bonded to oxygen atoms, wherein the oxygen atoms are bound to vanadium atoms and a monovalent organic group.

Suitable sources of vanadium include vanadium oxides such as $V_2O_3$, $V_2O_5$, $V_2O_4$ and $VOSO_4$; vanadium halides, such as $VCl_3$; and vanadium oxyhalides, such as $VOCl_3$. The amount of vanadium and phosphorus or arsenic oxides to be used in the synthesis is such that the molar ratio of the vanadium:phosphorus or vanadium:arsenic in the final compound ranges from about 1:1 to about 3:1 and more preferably ranges from about 1.5:1 to about 2:1. The variable a represents the molar amount of vanadium oxide in the composition. Based on the required vanadium ratio, a ranges from about 1 to about 3 and more preferably from about 1.5 to about 2.0.

The amount of oxygen coordinated with vanadium is such that the molar ratio of vanadium:coordinated oxygen ranges from about 1 to about 2. The variable b represents the molar amount of oxygen coordinated only with vanadium in the composition. Based on the required coordinated oxygen ratio, b ranges from about 1.0 to about 2.0.

The vanadium atoms of the final composition have an average oxidation state (m) ranging from about 3.5 to about 5.0. and more preferably ranging from about 4.0 to about 5.0. The vanadium oxidation state depends on the specific synthesis conditions chosen. For a specific vanadium oxidation state, the negative charge on the molecular anion is represented by the expression $(2ab+2)-ma$. The positive charge on the cation in the composition is represented by the expression $(x+y)$. For a charge balanced compound to exist, the total positive charge on the cation must equal the total negative charge on the molecular anion. Thus, $(x+y)$ must equal $(2ab+2)-ma$. For example, where the molar amount of vanadium oxide, a, equals 2, and the molar amount of coordinated oxygen, b, equals 2 and the average oxidation state of vanadium equals 4, then the relationship $(2ab+2)-ma=(x+y)$ dictates that the number of cations in the composition is 2.0. However, $(x+y)$ cannot equal zero and typically ranges from about 1 to about 2 also x cannot equal zero.

Compounds of the invention may have one or more solvent molecules incorporated therein depending on the particular method of preparation used or the solvent employed. The compounds, however, need not contain solvent. The number of solvent molecules incorporated in the compound preferably ranges from about 0.1 to about 2.0. Suitable solvents are selected from water, methanol, ethanol, acetone and the like, or mixtures thereof.

Compounds of the invention may be prepared by several methods. One such method is hydrothermal synthesis where a solid vanadium source is combined with an aqueous suspension or solution of, for example $V_2O_3$, a phosphonic or phosphoric acid and an alkyl ammonium cation salt such as a hydroxide or halide salt. The organic cation, alkyl ammonium cation, in this case, acts to direct the formation of the molecular anion in the compound. The pH of the mixture is adjusted by adding a base and ranges from about 4.0 to about 14.0 and more preferably from about 4.0 to about 10.0. Suitable bases for adjusting the pH include alkali metal hydroxides and alkylammonium hydroxides. The resultant mixture is contained in a reaction vessel capable of sustaining pressures above atmospheric pressure. The pressure in the reaction vessel is based on the total volume of reactants in the vessel and the reaction temperature. The reaction temperatures range from about 50° C. to about 250° C. However, if the ratio of the volume of reactants in the vessel: the fill volume is from about 0.50 to about 0.90, then the reaction temperature is preferably below about 250° C. Any suitable reaction vessel, equipped with a heating means, may be used such as a teflon lined stainless steel autoclave.

Once the compound is formed, it may be recovered from the reaction medium by any suitable technique. However, when water is used as the solvent, the compound is preferably recovered by cooling and filtering the reaction mixture to obtain the compound and then washing and drying the compound. The final compound may be anhydrous or contain water of crystallization, represented by $.nH_2O$ in the general formula. The moles of water, n, ranges from zero to a positive number and more preferably ranges from about 0.1 to about 2.0.

The heteropolyoxo vanadium oxide compounds provided herein are useful in catalyzing hydrocarbon oxidation reactions, such as, the oxidation of butane to maleic anhydride. The compound may be contacted with a hydrocarbon under oxidation reaction catalytic conditions by methods known to those skilled in the art.

The following examples illustrate particular embodiments of the invention. The examples illustrate modifications of the invention and should not be construed as limiting the scope thereof. All parts and percentages are given in weight unless otherwise noted.

Example 1

Synthesis of $(CH_3)_4N_{1.125}H_{0.375}(VO_2)_2(C_6H_5PO_3).1.05H_2O$ $C_6H_5PO_3H_2$ (0.952 g, 6 mmol), $V_2O_3$ (0.150 g, 1 mmol) and $V_2O_5$ (0.182 g, 1 mmol) were transferred into a Teflon lined autoclave. Distilled water (approximately 2 ml) was added followed by $(CH_3)_4NOH$ (3.0 g, 25% in water). The total fill volume of the autoclave was adjusted to 60% of the total volume by adding distilled water. The mixture was heated at 200° C. for 4 days, and the reaction product was cooled in air, suction filtered, washed several times with distilled water and air dried. Dark brown hexagonal prismatic crystal compounds (0.68 g) of the above formula were collected in approximately 80% yield (based on moles of vanadium).

A chemical analysis of the crystals gave the following composition data (values are in wt. %):

| Observed | Calculated Based on $C_{84}H_{168.8}N_9V_{16}P_8O_{64.4}$ |
| --- | --- |
| C 30.41 | C 29.69 |
| H 4.93 | H 5.01 |
| N 3.80 | N 3.71 |
| V 24.56 | V 23.98 |
| P 7.47 | P 7.29 |

The vanadium oxidation state (m), determined by redox titration was 4.22; The main absorption bands in the IR spectrum gave (solid/KBr pellet): m [cm$^{-1}$](s), 1636 (m), 1486 (s), 1437 (m), 1119 (s), 1061 (s), 995 (vs), 930 (s), 760 (m), 720 (s), 700 (s). Thermogravimetric analysis gave n = 1.05.

Structural Analysis of $(CH_3)_4N_{1.125}H_{0.375}(VO_2)_2(C_6H_5PO_3)$ $1.05H_2O$ The compound formed in Example 1 was further characterized by determining its structure via single crystal X-ray crystallography. The compound was found to be monoclinic, space group $C_2/c$ (No. 15) with a = 18.363(2), b = 30.153(6), c = 26.593(4), b = 101.03(1)Å, V = 14,452(4) Å3, and Z = 4. X-ray structural analysis revealed the presence of $(CH_3)_4N^+$ and $H+$ cations, waters of crystallization and discrete $(VO_2)_2(C_6H_5PO_3)$ molecular anions.

The structure of the molecular anion consists of four structural units each containing four square based pyramids of oxygen and vanadium atoms where the vanadium atom is in the center of the pyramid. The pyramids join together to form tetramers. Four tetramers, connected by eight $C_6H_5PO_3$ groups via corner-sharing oxygen atoms, form a tetramer ring (see FIG. 1). The monovalent organic group is bonded to the phosphorus atoms and point away from the center of the ring. The atoms of the tetramer ring are coplanar within 0.34 Å. The ring has an inside diameter of about 4 Å at the narrowest point and about 7 Å at the widest point.

Example 2

Synthesis of $(CH_3)_4N_{1.0}H_{0.8}(VO_2)_2(CH_3PO_3).1.4H_2O$ $CH_3PO_3H_2$ (1.152 g, 12 mmol), $V_2O_3$ (0.300 g, 2 mmol), and $V_2O_5$ (0.364 g, 2 mmol) were transferred into a Teflon lined autoclave. Distilled water (approximately 2 ml) was added followed by $(CH_3)_4NOH$ (6.4 g, 25% in water). The total fill volume of the autoclave was adjusted to 80% of the total volume by adding distilled water. The mixture was then heated at 200° C. for 2 days, and the reaction product was cooled in air, suction filtered, washed several times with distilled water and air dried. Dark, prismatic crystal compounds of the above formula (0.60 g) were collected in approximately 42% yield (based on the moles of vanadium).

A chemical analysis of the crystals gave the following composition data (values are in wt. %):

| Observed | Calculated Based on $C_{40}H_{148}N_8V_{16}P_8O_{67}$ |
| --- | --- |
| C 16.11 | C 16.70 |
| H 5.75 | H 5.19 |
| N 3.80 | N 3.90 |
| V 28.13 | V 28.34 |
| P 8.34 | P 8.61 |

The vanadium oxidation state (m), determined by redox titration was 4.2.

The main absorption bands in the IR spectrum gave (solid/KBr pellet): m [cm$^{-1}$]=3399 (s), 3010 (M), (m), 1480 (s), 1410 (m), 1300 (S), 1110 (s), 1050 (s), 1000 (VS), 970 (VS), 935 (vs), 770 (m), 700 (s), (s), 570 (S), 530 (S), 485 (S), 435 (M).

Example 3

Synthesis of $(CH_3)_4N_{1.0}H_{1.0}(VO_2)_2(C_2H_5PO_3).2.0H_2O$ $C_2H_5PO_3H_2$ (1.120 g, 10 mmol) and $V_2O_5$ (0.560 g, 3.08 mmol) were transferred into a Teflon lined autoclave. Distilled water (approximately 2 ml) was added followed by $(CH_3)_4NOH$ (6.0 g, 25% in water). The total fill volume of the autoclave was adjusted to 50% of the total volume by adding distilled water. The mixture was heated at 200° C. for 16 hours and the reaction product was cooled in air, suction filtered, washed several times with $CH_3CN$ and air dried. Deep blue, prismatic crystal compounds (1.06 g) of the above formula were collected in approximately 89% yield (based on the wt. % of vanadium).

A chemical analysis of the crystals gave the following composition data (values are in wt. %):

| Observed | Calculated Based on $C_6H_{22}NV_2PO_9$ |
|---|---|
| C 19.12 | C 18.71 |
| H 5.45 | H 5.76 |
| N 3.67 | N 3.64 |
| V 26.47 | V 26.46 |
| P 8.01 | P 8.04 |

The main absorption bands in the IR spectrum gave (solid/KBr pellet): m [cm$^{-1}$]=3400 (s), 3200 (w), 2920 (w), 1635 (m), 1480 (s), 1450 (m), 1070 (w), 1030 (w), 1100 (s), 1040 (s), 1000 (vs), 970 (vs), (m), 700 (m), 620 (m), 530 (s), 500 (m), 440 (m).

Example 4

Synthesis of $(CH_3)_4N_{1.0}H_{1.0}(VO_2)_2(C_3H_7PO_3)\ 2.0H_2O$ $C_3H_7PO_3H_2$ (1.489 g, 12 mmol), $V_2O_3$ (0.300 g, 2 mmol), and $V_2O_5$ (0.364 g, 2 mmol) were transferred into a Teflon lined autoclave. Distilled water (approximately 2 ml) was added followed by $(CH_3)_4NOH$ (5.0 g, in water). The total fill volume of the autoclave was adjusted to 75% of the total volume by adding distilled water. The mixture was heated at 200° C. for hours. The product was cooled in air, suction filtered, washed several times with $CH_3CN$ and air dried. Deep blue crystal compounds (1.25 g) were collected in approximately 89% yield (based on the moles of vanadium).

A chemical analysis of the crystals gave the following composition data (values are in wt. %):

| Observed | Calculated Based on $C_7H_{24}NV_2PO_9$ |
|---|---|
| C 22.12 | C 21.89 |
| H 6.36 | H 6.30 |
| N 3.61 | N 3.61 |
| V 25.80 | V 26.52 |
| P 8.08 | P 8.06 |

Example 5

Synthesis of $[(C_2H_5)_4N]_{0.75}H_{1.25}(VO_2)_2(C_6H_5PO_3).0.5H_2O$ $C_6H_5PO_3H_2$ (0.952 g, 6 mmol), $V_2O_5$ (0.364 g, 2 mmol) were transferred into a Teflon lined autoclave. Distilled water (approximately 2 ml) was added followed by $(C_2H_5)_4NOH$ (3.58 g, 40% in water). The total fill volume of the autoclave was adjusted to 70% of the total volume by adding distilled water. The mixture was heated at 200° C. for 2 days. The product was cooled in air, suction filtered, washed several times with distilled water and air dried. Deep blue, prismatic crystal compounds (0.41 g) were collected in approximately 48% yield (based on moles of vanadium).

A chemical analysis of the crystals gave the following composition data (values are in wt. %):

| Observed | Calculated Based on $C_{12}H_{22.25}N_{0.75}V_2PO_{7.5}$ |
|---|---|
| C 32.94 | C 34.36 |
| H 5.06 | H 5.35 |
| N 3.21 | N 2.50 |
| V 24.80 | V 24.29 |
| P 7.31 | P 7.38 |

Example 6

Synthesis of $(C_3H_7)_4N_{0.5}H_{1.5}(VO_2)_{1.5}(C_6H_5PO_3).0.5H_2O$ $C_6H_5PO_3H_2$ (0.952 g, 6 mmol) and $VOSO_4.3H_2O$ (0.651 g, 3 mmol) were transferred into a Teflon lined autoclave. Distilled water (approximately 2 ml) was added followed by 8.2 g $(C_3H_7)_4NOH$ (8.2 g, 1M in water). The total fill volume of the autoclave was adjusted to 70% of the total volume by adding distilled water. The mixture was heated at 200° C. for 2 days. The product was cooled in air, suction filtered, washed several times with $CH_3CN$ and air dried. Blue crystal compounds (0.70 g) were collected in approximately 91% yield (based on the moles of vanadium).

A chemical analysis of the crystals gave the following composition data (values are in wt. %):

| Observed | Calculated Based on $C_{24}H_{43}NV_3P_2O_{13}$ |
|---|---|
| C 37.31 | C 37.51 |
| H 5.47 | H 5.64 |
| N 1.80 | N 1.82 |
| V 20.21 | V 19.89 |
| P 8.52 | P 8.06 |

The main absorption bands in the IR spectrum gave (solid/KBr pellet) n [cm$^{-1}$]: 3420 (s), 3225 (w), (m), 2925 (w), 2860 (w), 1640 (w), 1680 (m), 1645 (m), 1650 (m), 1440 (m), 1380 (w), 1130 (vs), 1110 (vs), 1030 (vs), 1010 (vs), 990 (vs), 905 (s), 755 (m), (s), 690 (s), 590 (m), 540 (s), 510 (s), 470 (w), 370 (w).

An x-ray structural analysis of the compound revealed the presence of $(CH_3)_4N+$ cations, waters of crystallization and discrete $[H_{12}(VO_2)_{12}(C_6H_5PO_3)_3]^{4-}$ anions.

Example 7

Synthesis of $(CH_3)_4N_{0.5}H_{1.5}(VO_2)_{1.5}(C_6H_5PO_3)\ 0.5H_2O$ $C_6H_5PO_3H_2$ (0.952 g, 6 mmol) and $V_2O_5$ (0.364 g, 2 mmol) were transferred into a Teflon lined autoclave. Distilled water (approximately 2 ml) was added followed by $(CH_3)_4NOH$ (1.50 g, 25% in water). The total fill volume of the autoclave was adjusted to 80% of the total volume by adding distilled water. The mixture was heated at 200° C. for 3 days. The product was cooled in air, suction filtered, washed several times with distilled water and air dried. Blue, platy crystal compounds (0.92 g) were collected in approximately 70% yield (based on the moles of vanadium).

A chemical analysis of the crystals gave the following composition data (values are in wt. %):

| Observed | Calculated Based on $C_{16}H_{27}NV_3P_2O_{13}$ |
|---|---|
| C 29.62 | C 29.29 |
| H 4.36 | H 4.15 |
| N 2.23 | N 2.13 |
| V 23.38 | V 23.29 |
| P 9.36 | P 9.44 |

It should be understood that the foregoing disclosure, description and examples are only illustrative of the invention. Various changes to the details of the invention will be apparent to the skilled worker, and may be made within the scope of the appended claims without departing from the spirit of the invention.

What is claimed is:

1. A composition of matter comprising heteropolyoxo vanadium compounds of the general formula:

$$(R'_4N)_xH_y(VO_b)_a(RQO_3)\cdot nH_2O$$

wherein $(VO_b)_a(RQO_3)$ is a molecular anion; R and R' selected from the group consisting of substituted or unsubstituted monovalent organic groups and mixtures thereof; Q is a phosphorus or arsenic atom; n is zero or a positive number; a is from about 1.0 to about 3.0; b is from about 1.0 to about 2.0; x and y are such that $(x+y)$ equals $(2ab+2)-ma$ where m is the oxidation state of the vanadium ranging from about 3.5 to about 5.0, and where $(x+y)$ and x cannot equal zero.

2. The composition of claim 1 wherein Q is phosphorus.

3. The composition of claim 2 wherein a is about 1.5 to about 2.0.

4. The composition of claim 2 wherein m is about 4 to about 5.

5. The composition of claim 2 wherein a equals 2; b equals 2; R is $C_6H_5$; and R' is $CH_3$.

6. The composition of claim 2 wherein a equals 2; b equals 2; R is $CH_3$; and R' is $CH_3$.

7. The composition of claim 2 wherein a equals 2; b equals 2; R is $C_2H_5$; and R' is $CH_3$.

8. The composition of claim 2 wherein a equals 2; b equals 2; R is $C_3H_7$; and R' is $CH_3$.

9. The composition of claim 2 wherein a equals 2; b equals 2; R is $C_6H_5$; and R' is $C_2H_5$.

10. The composition of claim 2 wherein a equals 1.5; b equals 2; R is $C_6H_5$; and R' is $C_3H_7$.

11. The composition of claim 2 wherein a equals 1.5; b equals 2; R is $C_6H_5$; and R' is $CH_3$.

Figure 3A:
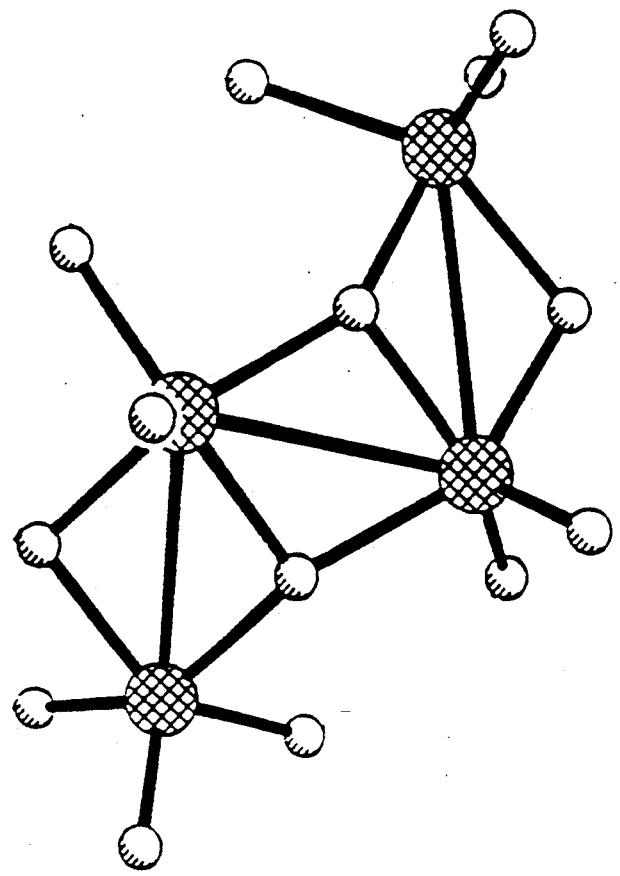
FIGS. 3a and 3b show a structural side view of the molecular anion of a heteropolyoxo vanadium compound of the present invention.
Figure 3B:
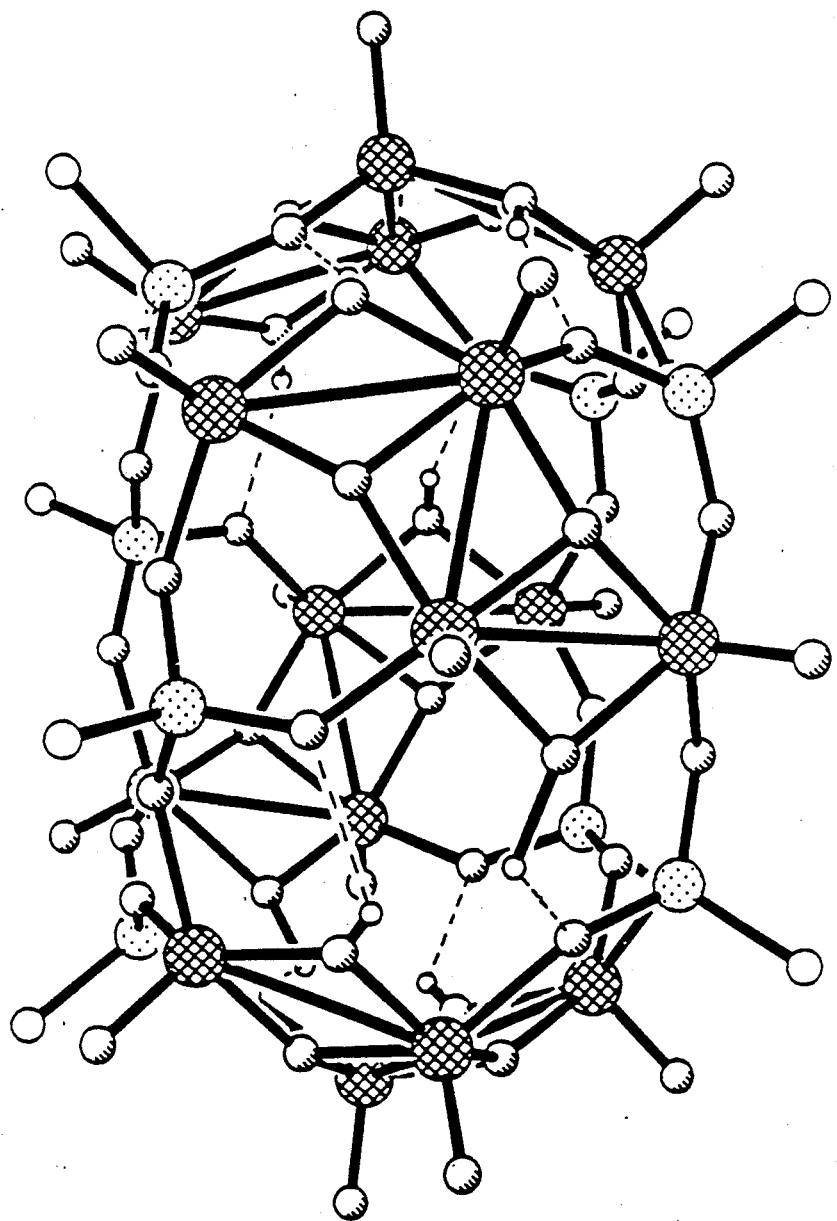
Figure 4:
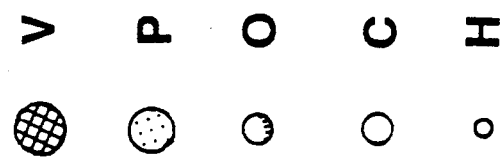
FIG. 4 shows a structural top view of the molecular anion in FIG. 3.
Figure 4:
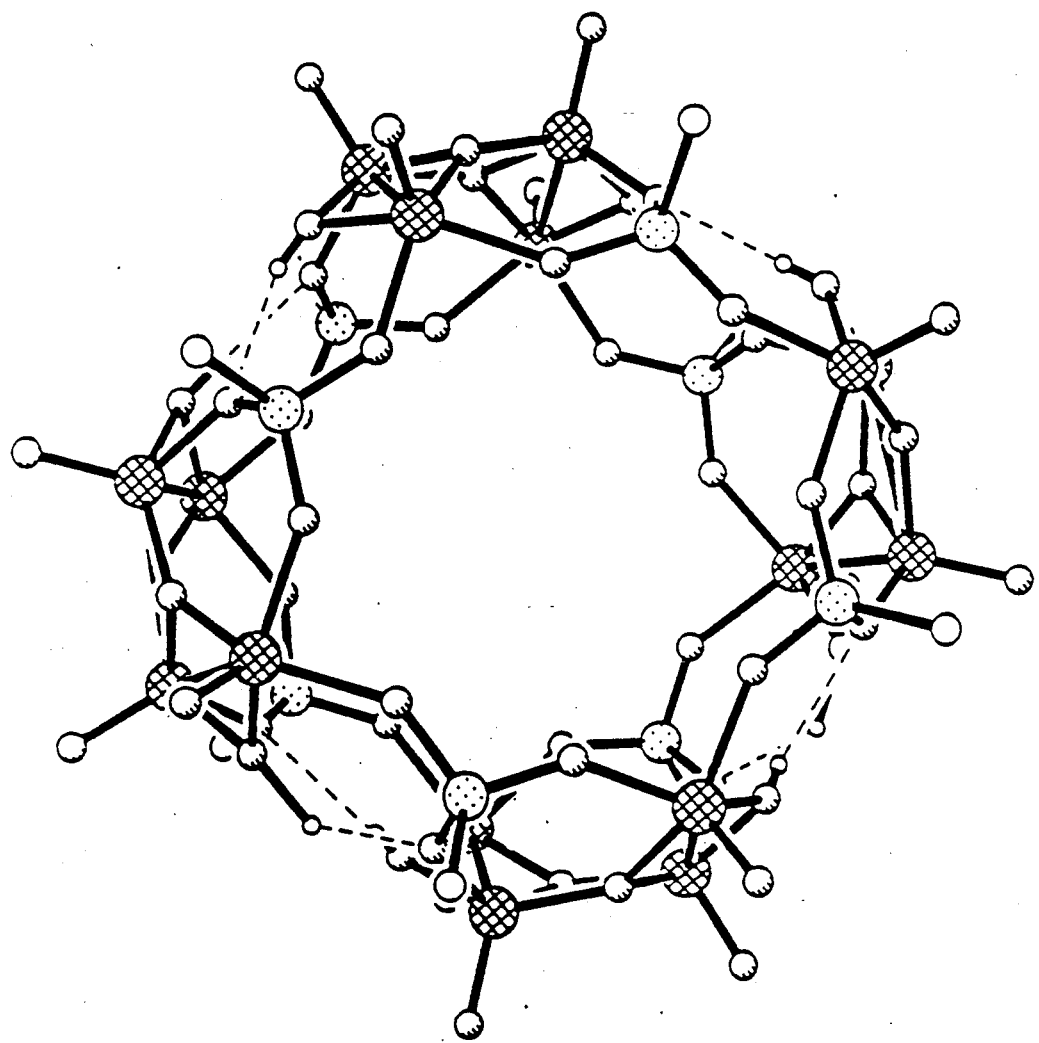

12. The composition of matter in claim 1 wherein the structure of the molecular anion corresponds to the structure shown in FIGS. 3 and 4 and characterized by x-ray crystallography as having a basic structural unit comprising four square base pyramids of oxygen and vanadium atoms; wherein a vanadium atom is in the center of the pyramid; wherein the pyramids are joined together to form tetramers; wherein four tetramers are joined together by eight $RQO_3$ groups via corner sharing oxygen atoms to form a ring having an inside diameter of about 4 Å at the narrowest point and about 7 Å at the widest point; wherein a monovalent organic group (R) is attached to a phosphorus or arsenic atom (Q); and wherein the monovalent organic group points away from the center of the ring.

Figure 5:
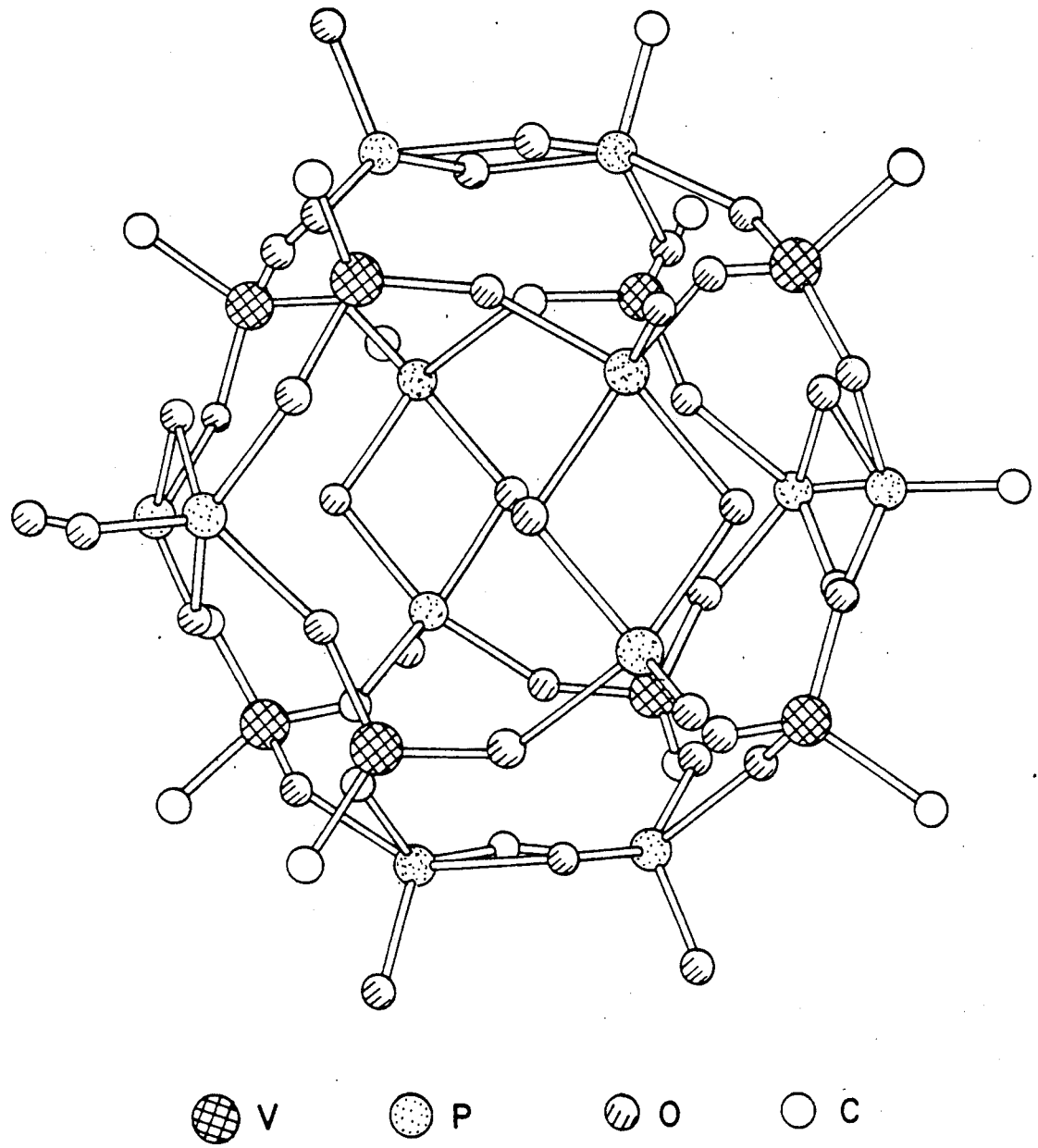
FIG. 5 shows a structural side view of the molecular anion of a heteropolyoxo vanadium compound of the present invention having a dodecahedron structure.

13. The composition of matter in claim 1 wherein the structure of the molecular anion corresponds to the dodecahedron structure shown in FIG. 5 and characterized by x-ray crystallography as containing twelve vanadium atoms and eight phosphorus or arsenic atoms (Q) occupying the twenty vertices of the dodecahedron; wherein each face of the dodecahedron contains (a) three square base pyramids of oxygen and vanadium atoms where a vanadium atom is in the center of the pyramid, (b) two $RQO_3$ groups and (c) two contiguous vanadium atoms.

* * * * *